US010675959B2

(12) United States Patent
Mankame et al.

(10) Patent No.: US 10,675,959 B2
(45) Date of Patent: Jun. 9, 2020

(54) HIERARCHICAL INFLATABLE STRUCTURES AND METHODS

(71) Applicant: GM GLOBAL TECHNOLOGY OPERATIONS LLC, Detroit, MI (US)

(72) Inventors: Nilesh D. Mankame, Ann Arbor, MI (US); Paul W. Alexander, Ypsilanti, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 330 days.

(21) Appl. No.: 15/595,501

(22) Filed: May 15, 2017

(65) Prior Publication Data

US 2018/0326825 A1    Nov. 15, 2018

(51) Int. Cl.
| B60J 7/12 | (2006.01) |
| A47C 4/54 | (2006.01) |
| B60J 7/08 | (2006.01) |
| A47C 7/50 | (2006.01) |
| A61B 17/00 | (2006.01) |
| B64G 1/22 | (2006.01) |

(52) U.S. Cl.
CPC .............. *B60J 7/1256* (2013.01); *A47C 4/54* (2013.01); *A47C 7/506* (2013.01); *B60J 7/085* (2013.01); *A61B 2017/00557* (2013.01); *B64G 2001/224* (2013.01)

(58) Field of Classification Search
CPC ........... B60J 7/1256; B60J 7/085; A47C 4/54; A47C 7/506; A61B 2017/00557; B65G 2001/224; F15B 15/10

USPC ............................................................ 141/1
See application file for complete search history.

(56) References Cited

U.S. PATENT DOCUMENTS

| 1,268,932 | A | * | 6/1918 | Corrigan | ............... | A61F 5/3769 |
| | | | | | | 602/36 |
| 1,567,973 | A | * | 12/1925 | Mendelson | ............ | A63H 13/16 |
| | | | | | | 446/198 |
| 4,724,560 | A | * | 2/1988 | Christie | ............... | A47C 27/081 |
| | | | | | | 5/644 |
| 4,819,547 | A | * | 4/1989 | Kukolj | .................. | F15B 15/103 |
| | | | | | | 92/153 |
| 5,311,706 | A | * | 5/1994 | Sallee | ..................... | E04C 3/005 |
| | | | | | | 52/2.18 |
| 6,328,385 | B1 | * | 12/2001 | Lau | .......................... | A47C 4/54 |
| | | | | | | 297/452.41 |
| 6,345,482 | B1 | * | 2/2002 | Warren | ................... | B64G 1/222 |
| | | | | | | 52/646 |

(Continued)

FOREIGN PATENT DOCUMENTS

CN            103976597 B  *  9/2016 ............. A47C 27/10

*Primary Examiner* — Timothy L Maust
*Assistant Examiner* — James R Hamomaki
(74) *Attorney, Agent, or Firm* — Lorenz & Kopf LLP (57) ABSTRACT

Products and methods are provided for inflatable structures. In various exemplary embodiments, an inflatable structure is provided with multiple variable chambers including a first variable chamber and a second variable chamber. A first boundary envelope defines the first variable chamber and a second boundary envelope defines the second variable chamber. The first and second boundary envelopes separate the first chamber from the second chamber. The first and second variable chambers are defined by an operative scale that may differ by an order of magnitude between the first and second variable chambers.

20 Claims, 6 Drawing Sheets

(56) References Cited

U.S. PATENT DOCUMENTS

| | | | | |
|---|---|---|---|---|
| 6,463,699 B1* | 10/2002 | Bailey | | E04C 3/005 |
| | | | | 138/115 |
| 6,598,250 B1* | 7/2003 | Pekar | | A47C 4/54 |
| | | | | 5/654 |
| 6,868,773 B2* | 3/2005 | Davis | | F15B 15/103 |
| | | | | 92/153 |
| 7,779,747 B2* | 8/2010 | Myers | | F15B 15/103 |
| | | | | 92/81 |
| 8,733,099 B2* | 5/2014 | Torres-Jara | | F03G 7/06 |
| | | | | 60/527 |
| 8,783,781 B1* | 7/2014 | McClure | | A47C 4/54 |
| | | | | 297/452.41 |
| 9,549,838 B2* | 1/2017 | Suarez | | A61F 5/41 |
| 9,664,210 B2* | 5/2017 | Ou | | F15B 15/10 |
| 9,835,184 B2* | 12/2017 | Bishop-Moser | | F15B 15/10 |
| 2002/0142119 A1* | 10/2002 | Seward | | A61L 29/126 |
| | | | | 428/36.9 |
| 2007/0273188 A1* | 11/2007 | Morrison | | A47C 4/54 |
| | | | | 297/284.3 |
| 2008/0238258 A1* | 10/2008 | Ishiguro | | H01L 41/0836 |
| | | | | 310/328 |
| 2010/0256540 A1* | 10/2010 | Yamashiro | | A61H 9/0078 |
| | | | | 601/44 |
| 2012/0161579 A1* | 6/2012 | Browne | | F15B 15/10 |
| | | | | 310/330 |
| 2014/0021768 A1* | 1/2014 | Chen | | A47C 4/54 |
| | | | | 297/452.41 |
| 2016/0048134 A1* | 2/2016 | Thomason | | A63F 13/98 |
| | | | | 700/275 |
| 2017/0067491 A1* | 3/2017 | Asai | | F15B 15/103 |
| 2018/0017088 A1* | 1/2018 | Asai | | B25J 9/142 |
| 2018/0252244 A1* | 9/2018 | Suzumori | | F15B 15/10 |
| 2019/0040880 A1* | 2/2019 | Fuyuki | | F15B 15/10 |

* cited by examiner

HIERARCHICAL INFLATABLE STRUCTURES AND METHODS

INTRODUCTION

The present disclosure generally relates to hierarchical inflatable structures and methods and more particularly, relates to inflatable structures adapted to differential pressurization of multiple variable chambers for variable deployment.

Inflatable structures such as balloons, inner tubes, flotation devices, and air mattresses have a container that holds air or another fluid. The container has a defined geometry to provide a desired shape that generally expands when inflated. As such, inflatable structures are generally provided as cushions, such as in the case of inner tubes or mattresses, or as buoyant containers, such as in the case of balloons or floatation devices.

Accordingly, it is desirable to provide inflatable structures for a broader range of applications. In addition, it is desirable to provide inflatable structures that serve additional functions. Furthermore, other desirable features and characteristics of inflatable structures will become apparent from the subsequent detailed description and the appended claims, taken in conjunction with the accompanying drawings and the foregoing technical field and background.

SUMMARY

Products and methods are provided for inflatable structures. In various exemplary embodiments, an inflatable structure is provided with multiple variable chambers including a first variable chamber and a second variable chamber. A first boundary envelope defines the first variable chamber and a second boundary envelope defines the second variable chamber. The first and second boundary envelopes separate the first variable chamber from the second variable chamber. The first and second variable chambers are defined by an operative scale that may differ by an order of magnitude between the first and second variable chambers.

In other exemplary embodiments, a method is provided for deploying an inflatable structure that has a first variable chamber and a second variable chamber. The first variable chamber is constructed with a first volume defined by a first boundary envelope. The second variable chamber is constructed with a second volume defined by a second boundary envelope. The second volume is separated from the first volume and the first and second volumes may differ in size by an order of magnitude.

In additional exemplary embodiments, an inflatable structure has multiple variable chambers including a first variable chamber and a second variable chamber. A pressure source is configured to inflate the inflatable structure. An inflation system is configured to inflate the first variable chamber to a first pressure and to inflate the second variable chamber to a second pressure by selectively connecting the pressure source with the first and second variable chambers. A first boundary envelope defines a first volume of the first variable chamber. A second boundary envelope defines a second volume of the second variable chamber. The first volume may be approximately ten times the second volume in magnitude. The second pressure may be greater than the first pressure so that multiple configurations or articulations of the inflatable structure are provided by selective pressurization of the multiple variable chambers.

BRIEF DESCRIPTION OF THE DRAWINGS

The exemplary embodiments will hereinafter be described in conjunction with the following drawing figures, wherein like numerals denote like elements, and wherein.

DETAILED DESCRIPTION

The following detailed description is merely exemplary in nature and is not intended to limit the subject matter of the application or its uses. Furthermore, there is no intention to be bound by any expressed or implied theory presented in the preceding introduction, summary or the following detailed description.

In accordance with the preferred embodiments described herein, inflatable structures may have desirable performance through the use of a skeleton and flesh type paradigm and hierarchical aspects. Multiple variable chambers may be used wherein the different chambers are separately inflated and have features at different operative scales. For example, exemplary embodiments may use variable chambers with different volumes as operative scales that may differ by an order of magnitude. Variable chambers may be actuated preferentially so that a relatively small scale variable chamber affects the overall performance of a relatively large scale variable chamber. The variable chambers may be actuated with a positive or a negative pressure source to inflate/deflate through changes in internal pressure. Design features such as inflation pressure, fluid flow into/out of/through the chamber, and inflated geometry of each variable chamber may be adapted to its respective function in the overall structure. The variable chambers may be pressurized at different levels, and different variable chambers may manage different aspects of performance. This results in inflatable structures whose geometry and/or properties can be changed or whose motion can be controlled on-the-fly. Large volume inflated structures may be packaged in small volumes when uninflated, and are quickly deployed by separate inflation of the variable chambers.

Figure 1:
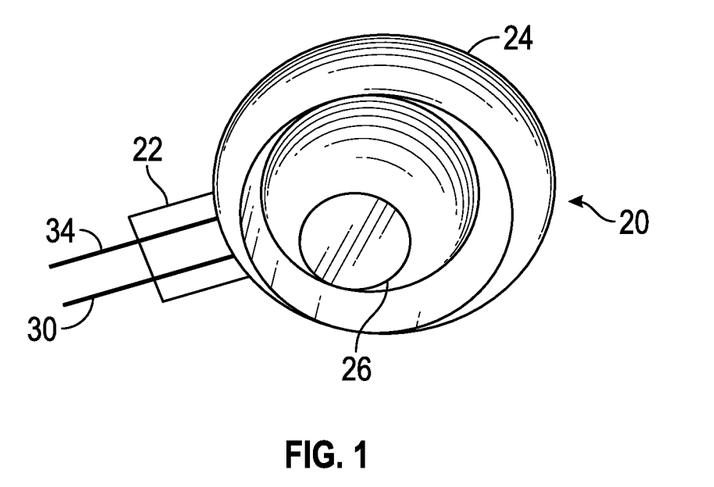
FIG. 1 is a schematic cross sectional illustration of an inflatable structure shown in an uninflated state, in accordance with an embodiment.
Figure 2:
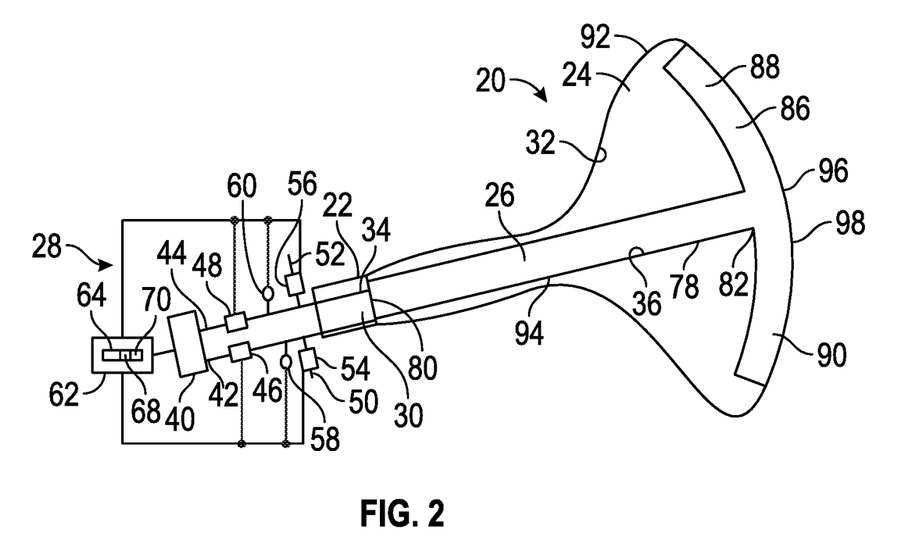
FIG. 2 is a schematic cross sectional illustration of the inflatable structure of FIG. 1 shown in a first state, in accordance with an embodiment.
Figure 3:
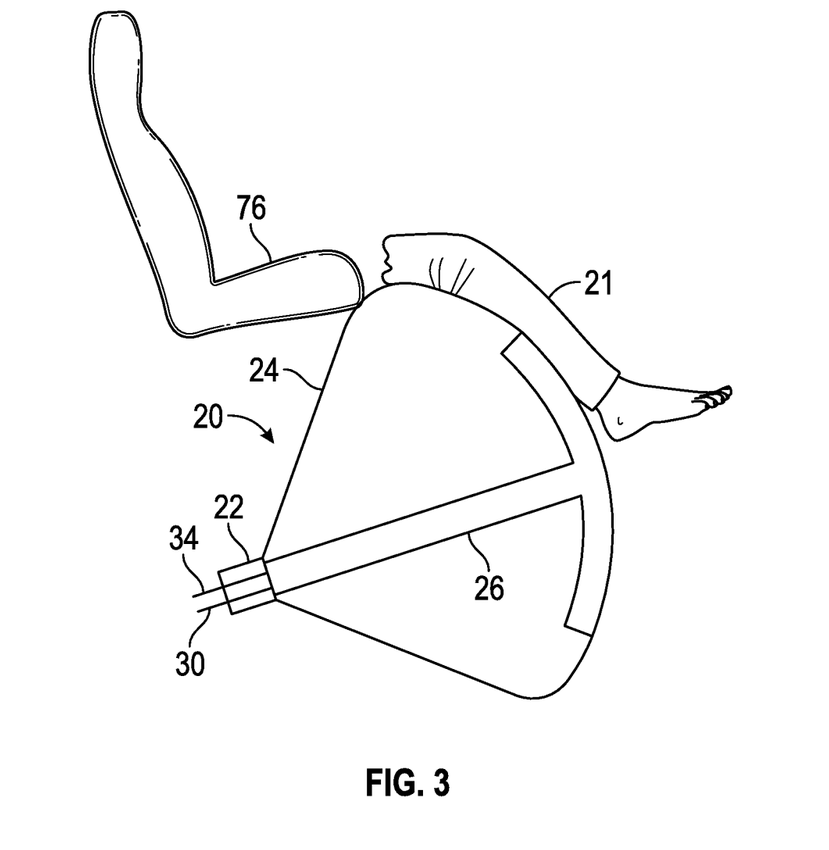
FIG. 3 is a schematic cross sectional illustration of the inflatable structure of FIG. 1 shown in a second state, in accordance with an embodiment.

In an exemplary embodiment as illustrated in FIGS. 1-3, an inflatable structure 20 includes a base 22 with connected multiple variable chambers including a first variable chamber 24 and a second variable chamber 26. The base 22 serves as an interface between the variable chambers 24, 26 and an inflation system 28 (omitted in FIGS. 1 and 3 for simplicity). The inflation system 28, or a portion thereof, may be housed within the base 22, or located remotely. As shown in FIG. 1 in an uninflated state, the inflatable structure 20 consumes a small volume compared to the inflated state of FIG. 3, and when uninflated is packaged as a compact unit. The base 22 includes a first nozzle 30 in open fluid communication with the inside 32 of the first chamber 24, and a second nozzle 34 in open fluid communication with the inside 36 of the second variable chamber 26.

The exemplary inflation system 28, which may be used in multiple embodiments, includes a pressure source 40, such as a compressor, vacuum pump, other vacuum source, or charged canister. The pressure source 40 is fluidly coupled with the first and second nozzles 30, 34 through the conduits 42, 44, respectively. Control valves 46, 48 are provided in the conduits 42, 44 respectively, to selectively connect/disconnect the nozzles 30, 34 with/from the pressure source 40, or to throttle flow to control downstream pressure for varying pressure in the variable chambers 24, 26. The inflation system 28 may supply pressure to the variable chambers or draw vacuum in the variable chambers, depending on the application. The conduits 42, 44 are fluidly coupled with exhaust/intake lines 50, 52 respectively, each including an exhaust/intake control valve 54, 56 respectively, to selectively release pressure from the variable chambers 24, 26 to the atmosphere for return of the variable chambers 24, 26 to uninflated states, or to selectively allow atmospheric pressure into the variable chambers 24, 26 to relieve vacuum and inflate the chambers 24, 26. Pressure sensors 58 and 60 are provided in the conduits 42, 44 respectively, to monitor pressure therein and to supply signals representative of the pressure to a controller 62. Each of the valves 46, 48, 54 and 56 is in electrical communication with the controller 62. As will be appreciated, the current embodiment employs an inflation system 28 configured to control the inflation of two variable chambers 24, 26 but any number of variable chambers may be used as dictated by the application. With additional variable chambers a corresponding number of inflation nozzles, valves and pressure sensors are provided, with the inflation system 28 configured to provide inflation/deflation through those nozzles. In some embodiments, the control valves 46, 48 are closed after inflation and the variable chambers 24, 26 are sealed. In some embodiments, one or more of the control valves 46, 48 remain open when the inflatable structure 20 is deployed and may be throttled to provide constant air flow to maintain the shape and pressure. Localized inflation and deflation within a large scale chamber may be effected through the inflation system 28. Flow into, out of, or through a chamber or a number of chambers may be provided for dynamic applications where transient local changes are desirable.

In a number of embodiments, the controller 62 comprises a computer system. In the depicted embodiment, the computer system of the controller 62 includes a processor 64, and memory 68. The processor 64 performs the computation and control functions of the controller 62, and may comprise any type of processor or multiple processors, single integrated circuits such as a microprocessor, or any suitable number of integrated circuit devices and/or circuit boards working in cooperation to accomplish the functions of a processing unit. During operation, the processor 64 executes one or more programs which may be contained within the memory 68 and, as such, controls the general operation of the controller 62 and the computer system of the controller 62 in executing the processes described herein. The memory 68 is any type of suitable memory. For example, the memory 68 may include various types of dynamic random access memory (DRAM) such as SDRAM, the various types of static RAM (SRAM), and the various types of non-volatile memory (PROM, EPROM, and flash). In certain examples, the memory 68 is located on and/or co-located on the same computer chip as the processor 64. In the depicted embodiment, the memory 68 stores the above-referenced program along with one or more stored values 70. It will similarly be appreciated that the computer system of the controller 62 may also otherwise differ from the embodiment depicted in FIG. 1, for example in that the computer system of the controller 62 may be coupled to or may otherwise utilize one or more remote computer systems and/or other control systems.

The inflatable structure 20 of the exemplary embodiment illustrated in FIGS. 1-3 involves a deployable leg support such as may be used to support the legs 21 of a person in a seated position. The base 22 may be disposed under a seat 76 so that when in the uninflated state of FIG. 1, the inflatable structure 20 is stowed in a compact form in a convenient location. The seat 76 may be in a vehicle such as a plane or automobile, or in any other environment. Inflation of the inflatable structure 20 includes opening the control valve 48 in response to a signal generated by the processor 64 of the controller 62, such as when selected by the seated individual. Deployment of the inflatable structure 20 is initiated with the second variable chamber 26 being inflated with pressure from the pressure source 40 through the conduit 44 and the nozzle 34. The second variable chamber 26 is configured with a beam 78 that is elongated and that extends generally horizontally, or at an incline relative to horizontal from a proximal end 80 at the base 22 to a distal end 82 opposite the proximal end. The second variable chamber 26 includes a support member 86 extending upward and downward from the distal end 82 of the beam 78 with an upper limb 88 and a lower limb 90. The beam 78 and the support member 86 include a common variable chamber 26 with an inside 32 carrying the same pressure in the beam 78 and in the support member 86. The controller 62 monitors the pressure at the inside 32 through the pressure sensor 60. The processor 64 accesses the design pressure from the storage values 70 and when the pressure as indicated by a signal from the pressure sensor 60 matches the design pressure, the control valve 48 is closed to maintain pressure. Following at least partial inflation of the second variable chamber 26, the processor 64 signals the control valve 46 to open. Pressure from the pressure source 40 enters the first variable chamber 24 through the conduit 42 and the nozzle 30. The first variable chamber 24 inflates around the second variable chamber 26 as shown in FIG. 3, in the shape of a leg support in front of the seat 76. The controller 62 monitors the pressure at the inside 32 of the first variable chamber 24 through the pressure sensor 60. The processor 64 accesses the design pressure from the stored values 70 and when the pressure as indicated by a signal from the pressure sensor 62 matches the design pressure, the control valve 46 is closed to maintain pressure and shape of the first variable chamber 24. In some embodiments, the control valves 46, 48 may remain open to supply constant air flow to maintain the pressure and shape. The exhaust valves 54, 56 remain closed during inflation.

In a number of examples, the first variable chamber 24 is defined by a boundary envelope 92 formed from a material in the desired geometric shape. The material of the boundary envelope 92 is bendable to package for storage purposes and may be expandable/stretchable. Non-limiting material examples include polyurethane, silicones, silicone based blends, and natural or synthetic elastomers. Similarly, the second variable chamber 26 is defined by a boundary envelope 94 formed from a bendable material in the desired geometric shape, and exhibits a non-stretchable/non-expandable construction or one that is substantially non-stretchable/non-expandable. Non-limiting material examples include polymers such as polyethylene, polypropylene, aliphatic or semi-aromatic polyamides, and may include embedded or laminated high tensile woven fabric. The boundary envelopes 92, 94 define separate variable chamber 24, 26. In some embodiments the boundary envelopes 92, 94 may be coextensive or connected at an interface 96 along the support member 86 on its side 98 opposite the beam 78.

In various embodiments, the second variable chamber 26 is inflated to a higher design pressure compared to the first variable chamber 24. This results in a higher stiffness of the boundary envelope 94 as compared to the boundary envelope 92. The volume of the first variable chamber 24 is larger as compared to that of the second variable chamber 26. For example, the volumes may differ by an order of magnitude where the first variable chamber may be ten times that of the second variable chamber. As a result, the inflatable structure 20 deploys upon pressurization of the second variable chamber 26, to a state that gives a perceivable impression of its size more quickly than if the inflatable structure were one variable chamber, or if the first variable chamber 24 were inflated first. Through the construction of the inflatable structure 20 a skeleton and flesh type paradigm is achieved where the second variable chamber 26 provides the supportive skeleton and the first variable chamber 24 provides the skin/flesh. The first variable chamber 24 is provided with a large volume at a low pressure for desirable characteristics such as comfort.

The second variable chamber 26 is provided with a low volume at higher pressure for quick deployment and structural support. Quick deployment means the inflatable structure 20 inflates to an intermediate state defined by the shape of the second boundary envelope 94, so that the size is perceivable and for quick gratification of the user. For example, the leg support function becomes useful when the second variable chamber 26 is inflated. The first variable chamber 24 is then inflated and its design attributes are directed toward providing comfort. For example, the use of high pressure in the second variable chamber 26 for support and stiffness may allow the pressure in the first variable chamber 24 to be set at a lower level. The structural shape and pressure of the second variable chamber 26 may be tuned for the desirable stiffness and the first variable chamber 24 may be directed to desirable load distribution or other load response characteristics. Hierarchical aspects of the inflatable structure 20 include volumes as an operative scale, where the volumes of the variable chambers 22, 24 may vary by an order of magnitude.

To deflate the inflatable structure 20, the exhaust valves 54, 56 are provided with a signal to open from the controller 62. For example, the individual using the inflatable structure 20 as a leg support may select deflation via a switch (not shown). The control valves 46, 48 remain closed during deflation. When uninflated, the inflatable structure 20 may be re-stowed under the seat 76. The inflatable structure 20 may include a retraction mechanism for controlled stowage. For example, torsion springs or other features may be used to assist in retraction and stowage.

Figure 4:
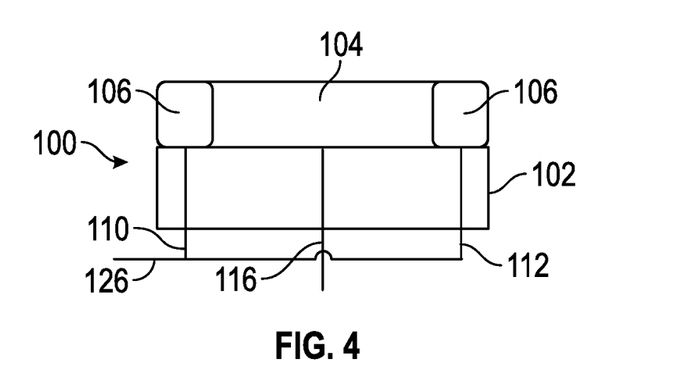
FIG. 4 is a schematic illustration of an inflatable structure shown in an uninflated state, in accordance with an embodiment.
Figure 5:
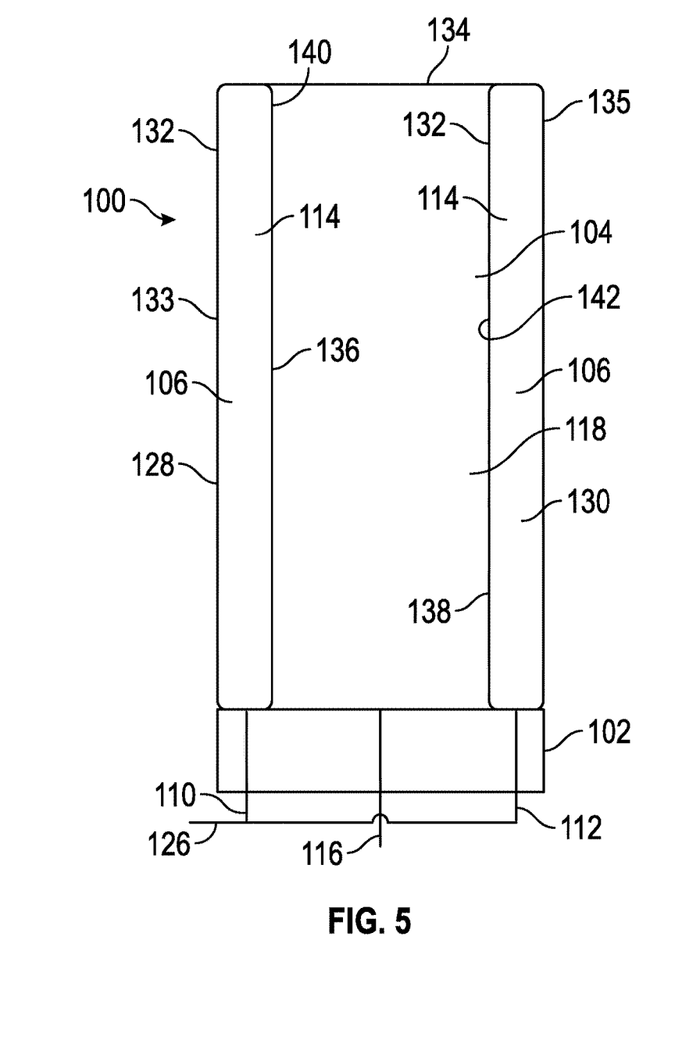
FIG. 5 is a schematic illustration of the inflatable structure of FIG. 4 shown in a first inflated state, in accordance with an embodiment.
Figure 6:
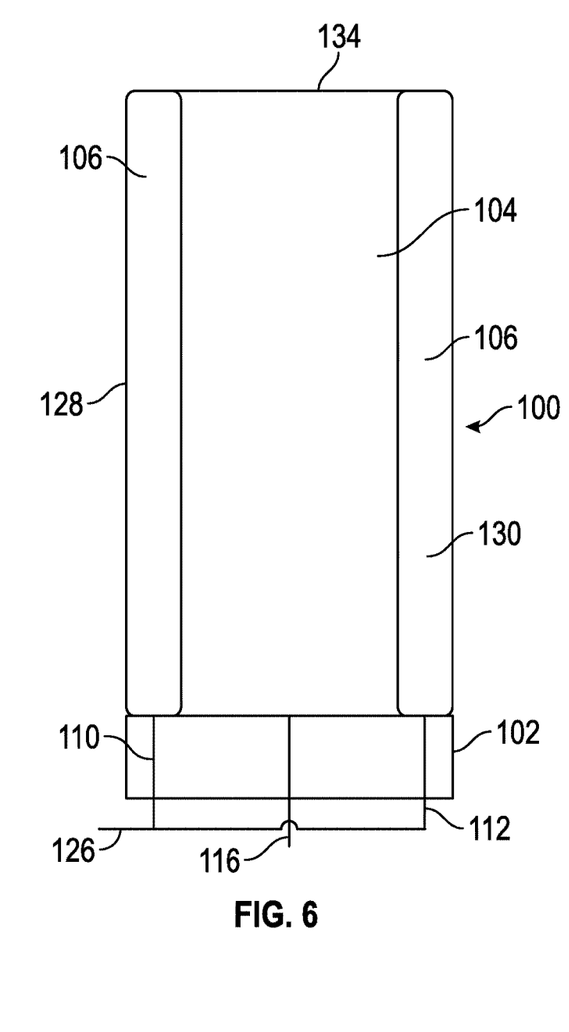
FIG. 6 is a schematic illustration of the inflatable structure of FIG. 4 shown in a second inflated state, in accordance with an embodiment.
Figure 7:
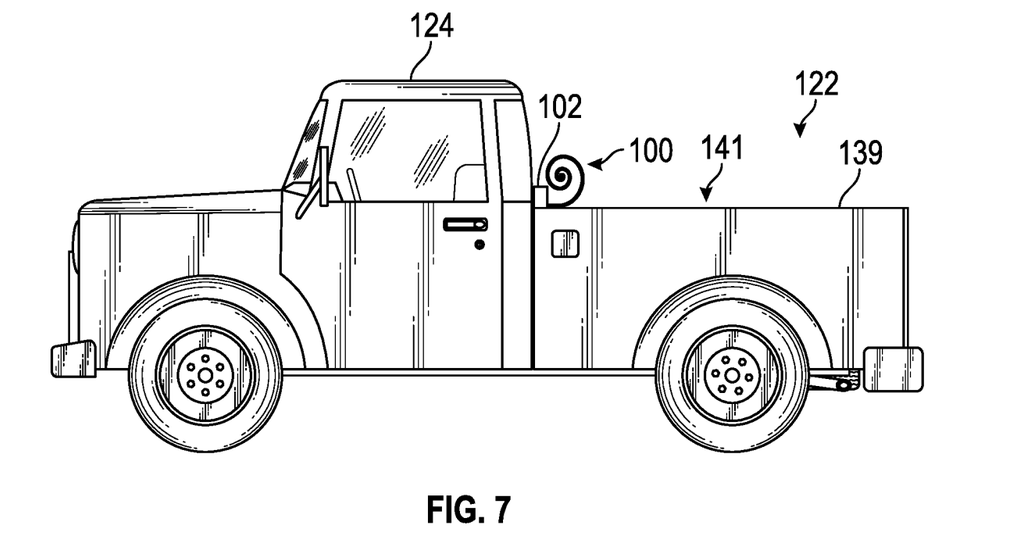
FIG. 7 is a schematic illustration of a pickup truck with the inflatable structure of FIG. 4 shown in an uninflated state.

In an exemplary embodiment as illustrated in FIGS. 4-8, an inflatable structure 100 includes a base 102 with connected multiple variable chambers including a first variable chamber 104 and a separate second variable chamber 106. The base 102 serves as an interface between the variable chambers 104, 106 and an inflation system such as the inflation system 28 of FIG. 1. As shown in FIG. 4, when uninflated, the inflatable structure 100 consumes a small volume compared to the inflated state of FIG. 5, and may be rolled up as shown in FIG. 7. The base 22 includes first and second nozzles 110, 112 in open fluid communication with the inside 114 of the second variable chamber 106, and a third nozzle 116 in open fluid communication with the inside 118 of the first variable chamber 104.

Figure 8:
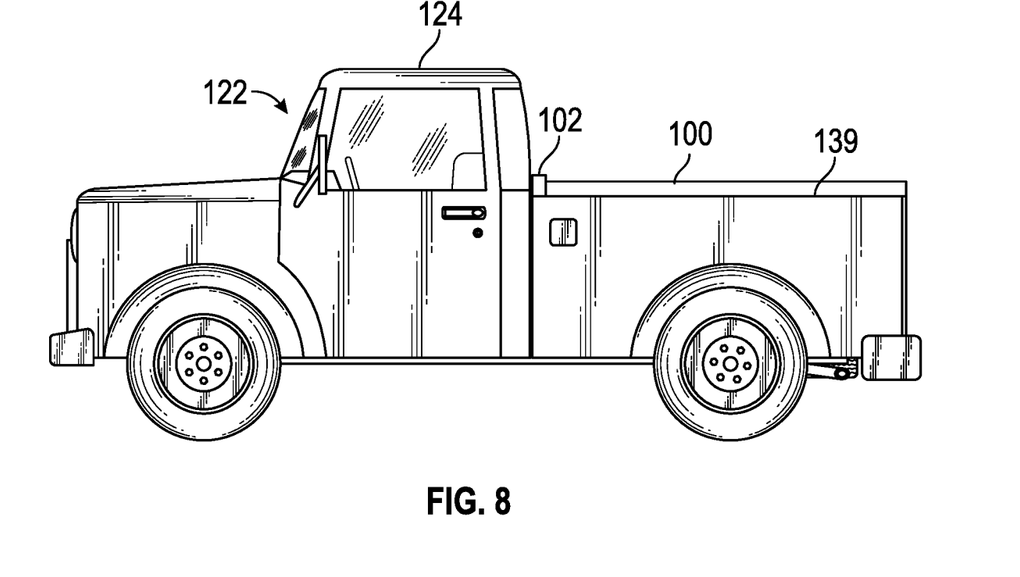
FIG. 8 is a schematic illustration of a pickup truck with the inflatable structure of FIG. 4 shown in an inflated state.

The inflatable structure 100 of the exemplary embodiment illustrated in FIGS. 4-8 involves a deployable curtain such as may be used to enclose the cargo area of a pickup truck 122 shown in FIGS. 7 and 8, or of another container, or which may be used to partition any area, or which may be used as a functional or styling surface that changes appearance through inflation level. In the exemplary embodiment, the base 102 may be disposed behind cab 124 so that when in the uninflated state of FIGS. 3 and 7, the inflatable structure 20 is stowed in a compact state such as in a rolled-up condition as shown in FIG. 7. Deployment of the inflatable structure 100 is initiated with the second variable chamber 106 being inflated with pressure such as from the pressure source 40 of FIG. 1, through the conduit 126 and the nozzles 110, 112. The second variable chamber 106 is configured as a pair of edge beams 128, 130 that are elongated and that extend from the base 102 and are disposed generally in a horizontal orientation, although other orientations are equally achieved. The edge beams 128, 130 are spaced apart and carry equal pressure due to their connection through the nozzles 110, 112 and the conduit 126. Alternatively, the edge beams 128, 130 may otherwise be connected inside or outside of the base 102. In some embodiments, the edge beams 128, 130 may be separately inflated. The edge beams 128, 130 control deployment of the inflatable structure 100 and provide rigid edges for stiffness and to facilitate attachment. The first variable chamber 104 fills the space defined by the second variable chamber 106 between the edge beams 128, 130.

In a number of examples, the second variable chamber 106 is defined by a boundary envelope 132 made from a material in the desired geometric shape to form the edge beams 128, 130. The boundary envelope 132 may include two pieces 133 and 135 defining tube-like edge beams 128, 130. The material of the boundary envelope 132 is bendable to bend for stowing purposes and may be non-expandable/non-stretchable, or substantially so. The first variable chamber 104 is defined by a boundary envelope 134 formed from a bendable material in the desired geometric shape, to bend and may exhibit a stretchable/expandable construction. The material examples listed above in describing FIGS. 1-3 are also non-limiting examples for use in the boundary envelopes 132, 134 of this exemplary embodiment. The boundary envelopes 132, 134 may be coextensive or connected with the boundary envelope 134 at interfaces 136, 138 along the sides 140, 142 of the second variable chamber 106.

As shown in FIGS. 5 and 8, the inflatable structure 100 is deployed and inflated to a first state with a first stiffness level. The second variable chamber 106 is pressurized to provide support for the inflatable structure 100 and the first variable chamber 104 is inflated to a lower pressure relative to the second variable chamber 106, sufficient to control sag and wind deflection. The second variable chamber 106 is inflated to a higher design pressure as compared to the first variable chamber 104. This results in a higher stiffness to the boundary envelope 132 as compared to the boundary envelope 134, which facilitates securing the inflatable structure to the pickup truck 122 such as along rail 139. The volume of the first variable chamber 104 is larger as compared to that of the second variable chamber 106. As a result, the inflatable structure 100 deploys more quickly than if the first variable chamber were inflated first, such as to rapidly cover the cargo area 141 of the pickup truck 122. Through the construction of this exemplary embodiment for the inflatable structure 100, a skeleton and flesh type paradigm is achieved where the second variable chamber 106 provides the supportive skeleton and the first variable chamber 104 provides the skin/flesh. Hierarchical aspects include the relative volumes of the first and second variable chambers 104, 106 as operative scales that may differ by an order of magnitude.

With reference to FIG. 6, the inflatable structure 100 is shown in a rigid state where the pressure is increased in the first variable chamber 104 as compared to FIG. 5. The design pressure in the first variable chamber 104 is such that the inflatable structure 100 presents high stiffness so as to better withstand wind, shifting loads and other stresses. In this embodiment, the boundary envelope 134 may be constructed of a material with limited expandability, such as those described above in relation to the embodiment of FIGS. 1-3. This embodiment may also provide desirable performance for use as a variable styling surface.

In a number of embodiments as illustrated in FIGS. 9-12, an inflatable structure 200 of an exemplary embodiment involves a deployable structure with multiple configurations. For example, a reversibly deployable structure functions in extension or contraction, or is controlled for varying load carrying capacity or gross motion/articulation. In general, the inflatable structure 200 has a first variable chamber 202, a second variable chamber 204, a third variable chamber 206 and a base 208. It should be appreciated that any number of variable chambers may be included depending on the number of deployed states desired. For example, controllable actions such as extension and contraction may be effected in different scales using any number of small scale variable chambers such as variable chambers 204 and 206, to affect the large scale variable chamber 202. The inflatable structure 200 is reversibly deployable with multiple helical variable chambers, such as variable chambers 204, 206, affecting the first variable chamber 202. The base 208 includes a first nozzle 210 in open fluid communication with the inside 212 of the first chamber 202, a second nozzle 214 in open fluid communication with the inside 216 of the second variable chamber 204, and a third nozzle 218 in open fluid communication with the inside 220 of the third variable chamber 206. It should be appreciated that multiple nozzles may be used for some or all of the variable chamber 202, 204, 206. The multiple nozzles may be located in different areas of a variable chamber 202, 204, 206, for faster pressure changes, and/or transient, localized pressure changes for temporary local state/property changes.

The exemplary inflation system 28 is modified to support three variable chambers and includes the pressure source 40, such as a compressor, vacuum pump, other vacuum source, or charged canister. The pressure source 40 is fluidly coupled with the first, second and third nozzles 210, 214, 218 corresponding to the chambers 202, 204, 206 respectively, through conduits 42, 44, 45 respectively. Control valves 46, 48, 49 are provided in the conduits 42, 44, 45 respectively, to selectively connect/disconnect the nozzles 210, 214, 218 with/from the pressure source 40. The conduits 42, 44, 45 are fluidly coupled with exhaust/intake lines 50, 52, 53 respectively, each including an exhaust/intake control valve 54, 56, 57 respectively, to selectively release pressure from the variable chambers 202, 204, 206 to the atmosphere, or to allow atmospheric pressure to enter. Pressure sensors 58, 60, 61 are provided in the conduits 42, 44, 45 respectively, to monitor pressure therein and to supply signals representative of the pressure to the controller 62. Each of the valves 46, 48, 49, 54 56 and 57 and each of the pressure sensors 58, 60, 61 is in electrical communication with the controller 62. In some embodiments, pressure, strain, force, or other sensors may be integrated into the boundary envelopes 236, 238, 240 of the variable chambers 202, 204, 206, respectively to monitor inflation. As will be appreciated, the current embodiment employs an inflation system 28 configured to control the pressure in three variable chambers 202, 204, 206 but any number of variable chambers may be used with a corresponding number of inflation nozzles and with the inflation system 28 configured to provide inflation/deflation through the number of nozzles.

Figure 9:
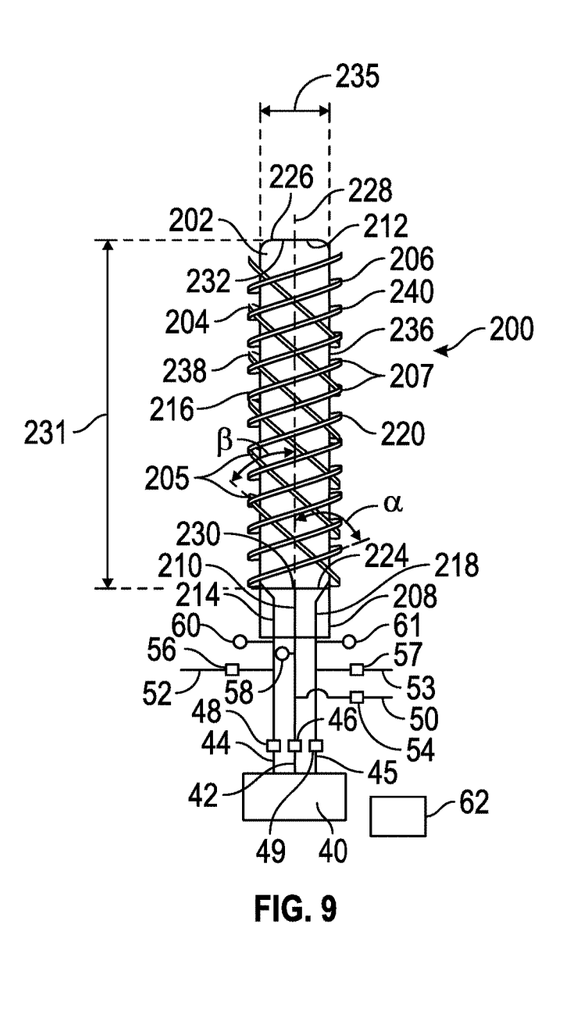
FIG. 9 is a schematic illustration of an inflatable structure shown in an uninflated state, in accordance with an embodiment.

The first variable chamber 202 has an elongated shape generally in the form of a cylinder with closed ends, and extends from a proximal end 224 at the base 208 to a distal end 226 opposite the proximal end 224. The second and third variable chambers 204, 206 are configured as overlapping double helix tubes wrapping around the first variable chamber 202. In this example, the second variable chamber 204 is shaped as a filament tube in a left-handed helix that extends from the base 208 approximately to the distal end 226. The third inflatable structure 206 is shaped as a filament tube in a right-handed helix that extends from the base 208 approximately to the distal end 226. As illustrated in FIG. 9 all variable chambers 202, 204, 206 of the inflatable structure 200 are not pressurized so that the inflatable structure 200 is in an unspooled state. In the unspooled state, the coils 207 of the third variable chamber 206 are disposed at an angle $\alpha$ relative to an axis 228 that extends from the center 230 of the base 208 through the center 232 of the distal end 226 and through the center of the first inflatable structure 202. Also in the unspooled state, the coils 205 of the second variable chamber 204 are disposed at an angle $\beta$ relative to the axis 228. The angle $\alpha$ is less than the angle $\beta$ so that when inflated, the second and third chambers 204, 206 effect different responses in the first variable chamber 202. In this example both the angles $\alpha$ and $\beta$ differ from fifty-seven degrees, with the angle $\alpha$ being less than fifty-seven degrees and the angle $\theta$ being greater than fifty-seven degrees. When inflated, the second and third variable chambers 204, 206 as helixes wrapped around a cylinder (the first variable chamber 202), attempt to move to fifty-seven degrees.

The first variable chamber 202 is defined by a boundary envelope 236 formed from a bendable material in the desired geometric shape. In this example the shape is that of a closed cylinder extending from the base 208. The material of the boundary envelope 236 is expandable/stretchable for reconfiguration purposes. The second variable chamber 204 is defined by a boundary envelope 238 formed from a bendable material in the desired geometric shape and is non-expandable/non-stretchable. The material examples listed above in describing FIGS. 1-3 are also non-limiting examples for the boundary envelopes 236, 238, 240 of this exemplary embodiment. In this example, the shape is that of a tube spiraling around the first variable chamber 202 in a left-hand (as viewed), helix-like manner. The third variable chamber 206 is defined by a boundary envelope 240 formed from a bendable material in the desired geometric shape. In this example, the shape is that of a tube spiraling around the first variable chamber 202 in a right-hand (as viewed), helix-like manner. The material of the boundary envelope 240 is non-expandable/non-stretchable. The second and third variable chambers 204, 206 overlap one another as they extend along the first variable chamber 202. The boundary envelopes 238 and 240 may be bonded, encapsulated by, or otherwise fixed to the boundary envelope 236 so that when they move upon pressurization, they draw the boundary envelope 236 along with them. In some embodiments, the boundary envelopes 238, 240 may be in contact with the boundary envelope 236, but not fixed so that they slide relative to one another.

Figure 10:
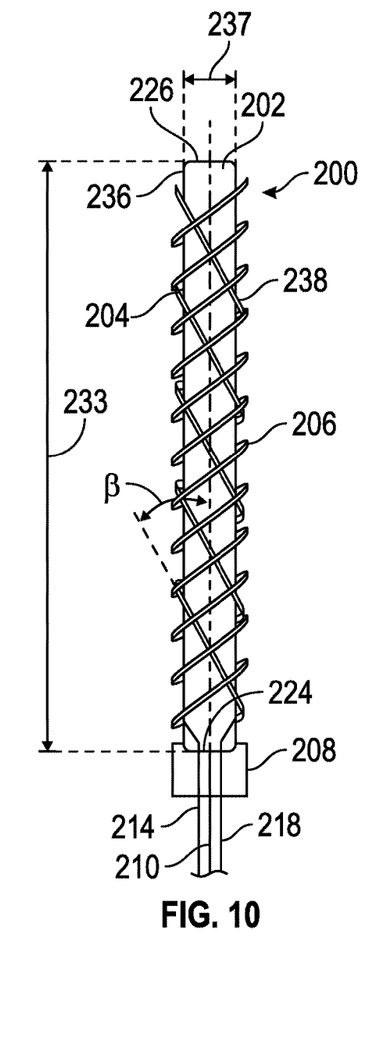
FIG. 10 is a schematic illustration of the inflatable structure of FIG. 9 shown in a first inflated state, in accordance with an embodiment.

Deployment of the inflatable structure 200 may be initiated in a number of variations such as to control deformation/articulation of the first variable chamber 202 and/or to increase stiffness of the inflatable structure 200. For example, as illustrated in FIG. 10, the control valve 48 may be opened by the controller 62 to pressurize the second variable chamber 204. The third variable chamber 206 remains uninflated. The first variable chamber 202 may not be inflated but the pressure at the inside 212 may increase as a result of contraction of the second variable chamber 204 due to its pressurization/spooling. Pressurization of the second variable chamber 204 acts to close the angle θ toward fifty-seven degrees. The response of the first variable chamber 202 includes its lengthening along the axis 228 from length 231 of FIG. 9 to length 233 of FIG. 10. The distal end 226 is repositioned a greater distance from the proximal end 224 than their distance of separation in FIG. 9. The response of the first variable chamber 202 also includes its contraction in width/diameter from diameter 235 of FIG. 9 to diameter 237 of FIG. 10. The angle θ is reduced relative to the unspooled state of FIG. 9. The boundaries 236 and 238 are in contact and fixed relative to each other so that the boundary envelope 236 moves with the boundary envelope 238 during spooling. As shown in FIG. 10, the inflatable structure 200 is extended and inflated to a first state with a first stiffness level that is relatively low due to no inflation of the first variable chamber 202 and the third variable chamber 206. The volume of the second variable chamber 204 is smaller as compared to the first variable chamber 202, such as by an order of magnitude, so that the inflatable structure deploys more quickly than if the first variable chamber 202 were inflated. Through this construction of the inflatable structure 200, a skeleton and flesh type paradigm is achieved where the second variable chamber 204 provides the supportive skeleton and the first variable chamber 202 provides the skin/flesh. Hierarchical aspects include the relative volumes of the first and second variable chambers 202, 204 as operative scales that may differ by an order of magnitude.

Figure 11:
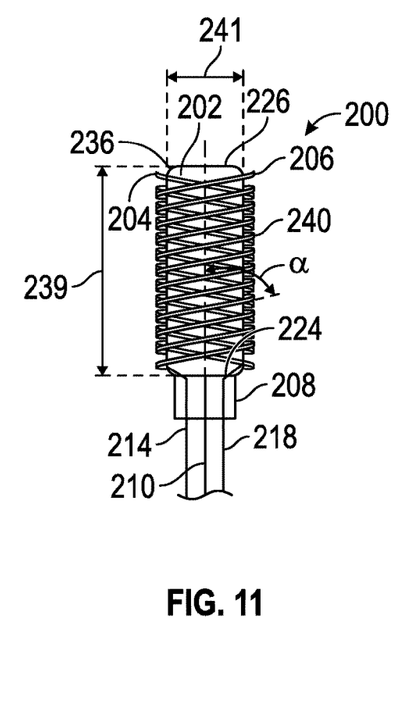
FIG. 11 is a schematic illustration of the inflatable structure of FIG. 9 shown in a second inflated state, in accordance with an embodiment.

In another example of deployment of the inflatable structure 200 as illustrated in FIG. 11, to deploy from the unspooled state of FIG. 9 the control valve 49 may be opened by the controller 62 to pressurize the third variable chamber 206. The second variable chamber 204 remains uninflated. The first variable chamber 202 may not be inflated but the pressure at the inside 212 may increase as a result of contraction of the third variable chamber 206 due to its pressurization/spooling. The response of the first variable chamber 202 includes its contraction or shortening along the axis 228 from the length 231 of FIG. 9 to the length 239 of FIG. 11. The distal end 226 is repositioned a shorter distance from the proximal end 224 than their distance of separation in FIG. 9. The response of the first variable chamber 202 includes its expansion in width/diameter from the diameter 235 of FIG. 9 to the diameter 241 of FIG. 11. The angle α is increased relative to the unspooled state of FIG. 9 as it moves toward fifty-seven degrees. The boundary envelopes 236 and 240 are in contact and fixed relative to each other during spooling so that the boundary envelope 236 moves with the boundary envelope 240. As shown in FIG. 11, the inflatable structure 200 is compressed and inflated to a state with a stiffness level that is relatively low due to no inflation of the first variable chamber 202 and the second variable chamber 204. The volume of the third variable chamber 206 is smaller as compared to the first variable chamber 202, such as by an order of magnitude, so that the inflatable structure deploys more quickly than if a change in inflation of the first variable chamber 202 were used. Through the construction of the inflatable structure 200 a skeleton and flesh type paradigm is achieved where the third variable chamber 206 provides the supportive skeleton and the first variable chamber 202 provides the skin/flesh. Hierarchical aspects include the relative volumes of the first and third variable chambers 202, 206 as operative scales that may differ by an order of magnitude.

Figure 12:
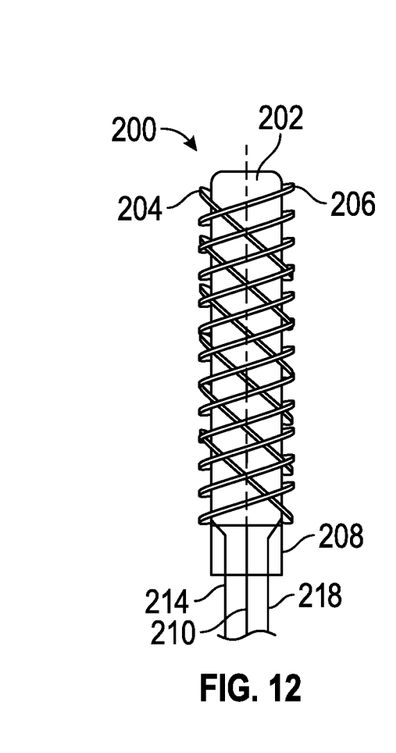
FIG. 12 is a schematic illustration of the inflatable structure of FIG. 9 shown in a third inflated state, in accordance with an embodiment.

In another example of deployment of the inflatable structure 200 as illustrated in FIG. 12, to deploy from the unspooled state of FIG. 9, the control valves 48 and 49 may both be opened by the controller 62 to pressurize the second variable chamber 204 and third variable chamber 206. The first variable chamber 202 may not be inflated but the pressure at the inside 212 may increase as a result of operation of the second and third variable chambers 204, 206 due to their pressurization/spooling. The response of the first variable chamber may be varied by changing the angles α and β, and the pressure level in variable chambers 204, 206. For example, setting α and β at angles that differ from fifty-seven degrees by the same amount, with one greater and one less than fifty-seven degrees, and setting the pressures the same, results in a response of the first variable chamber 202 with substantially no change in length 231 or diameter 235 as compared to the unspooled state of FIG. 9. This results from offsetting spooling action of the second and third variable chambers 204, 206, and increases the pressure in the first variable chamber 202. The boundaries 236, 238 and 240 are in contact and fixed relative to each other during spooling. As shown in FIG. 12, the inflatable structure 200 is inflated to a state with a relatively high stiffness level with no inflation of the first variable chamber 202. The volume of the second and third variable chambers 204, 206 are smaller as compared to the first variable chamber 202 so that the inflatable structure 200 deploys more quickly than if a change in inflation of the first variable chamber 202 was used. Stiffness may be further increased by inflation of the first variable chamber 202. Through the construction of the inflatable structure 200 a skeleton and flesh type paradigm is achieved where the second and third variable chambers 204, 206 provide the supportive skeleton and the first variable chamber 202 provides the skin/flesh.

Figure 13:
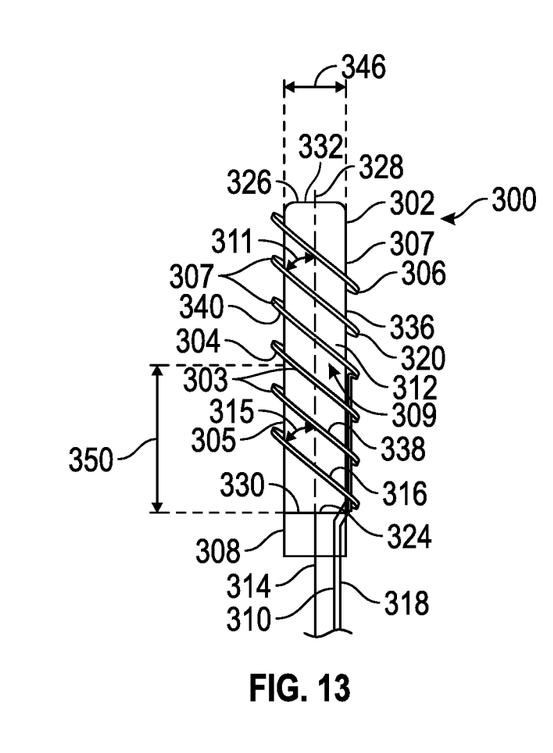
FIG. 13 is a schematic illustration of an inflatable structure shown in an uninflated state, in accordance with an embodiment.
Figure 14:
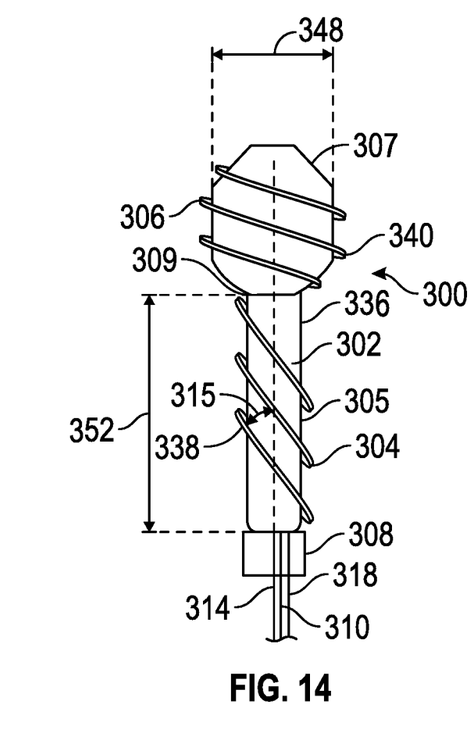
FIG. 14 is a schematic illustration of the inflatable structure of FIG. 13 shown in an inflated state, in accordance with an embodiment.

In a number of embodiments as illustrated in FIGS. 13-14, an inflatable structure 300 of an exemplary embodiment involves a deployable structure with multiple configurations. For example, the inflatable structure is reconfigured to different shapes for different functions and/or appearances. In general, the inflatable structure 300 has a first variable chamber 302, a second variable chamber 304 wrapped along a segment 305 of the first variable chamber 302, a third variable chamber 306 wrapped along a segment 307 of the first variable chamber 302, and a base 308. The base 308 includes a first nozzle 310 in open fluid communication with the inside 312 of the first chamber 302, a second nozzle 314 in open fluid communication with the inside 316 of the second variable chamber 304, and a third nozzle 318 in open fluid communication with the inside 320 of the third variable chamber 306.

The exemplary inflation system 28 as modified for the embodiment of FIG. 9 may be used with the pressure source 40 selectively fluidly coupled with the first, second and third nozzles 310, 314, 318. As will be appreciated, the current embodiment employs an inflation system 28 configured to control the inflation of three variable chambers 302, 304, 306 but any number of variable chambers may be used with a corresponding number of inflation nozzles and the inflation system 28 configured to provide inflation/deflation through those nozzles.

The first variable chamber 302 has an elongated shape and extends from a proximal end 324 at the base 308 to a distal end 326 opposite the proximal end 324. In the unpressurized state of FIG. 13 the first variable chamber 302 is generally in the shape of a closed cylinder. The second and third variable chambers 304, 306 are configured as staged helical tubes wrapping around the first variable chamber 302. In this example, the second variable chamber 204 extends from the base 308 to a transition segment 309 that is approximately half way between the proximal end 324 and the distal end 326. The third inflatable structure 306 extends from the transition segment 309 approximately to the distal end 326. The transition segment 309 is the part of the first variable chamber 302 where the coils of the second variable chamber 304 end and the coils of the third variable chamber 306 start. It should be understood that the segments 305, 307 wrapped by the second and third variable chambers 304 and 306, may be separated by a segment 309 that is not wrapped by a secondary chamber. Such a segment 309 may have a local fiber reinforcement or other mechanism that prevents it from expanding significantly during normal operation of the overall inflatable structure 300.

As illustrated in FIG. 13 all variable chambers 302, 304, 306 of the inflatable structure 300 are not pressurized and the inflatable structure 300 is in the cylindrical shape. The second and third variable chambers 304, 306 provide a variable restraint against radial expansion of the first variable chamber 302. When the second variable chamber 304 and/or the third variable chamber 306 is pressurized, it restrains the first variable chamber 302. The radial restraint provided by the second and/or third variable chamber 304, 306 may be switched off for a given variable chamber by leaving the variable chamber unpressurized. The radial restraint provided by the second and/or third variable chamber 304, 306 may be switched on for a given variable chamber by pressurizing the respective variable chamber. For example, as illustrated in FIG. 14, the second variable chamber 304 is pressurized and the third variable chamber 306 is unpressurized. When the first variable chamber 302 is pressurized with the second variable chamber 304 pressurized, the segment 305 of the first variable chamber 302 is restrained in the radial direction so that its diameter 346 is restricted from expanding by the individual coils 303 of the second variable chamber 304. When the first variable chamber 302 is pressurized with the third variable chamber 306 unpressurized, the segment 307 of the first variable chamber 302 is not restrained in the radial direction so that its diameter 346 may expand to the diameter 348 in FIG. 14. The amount of restraint provided by the second or third variable chamber 304, 306 is variable depending on the pressure level. For example, an intermediate level of expansion may be provided by partially pressurizing the second and/or third variable chamber 304, 306. Also for example, contraction of the first variable chamber 302 may be effected through higher pressure in the second and/or third variable chamber 304, 306. In the unpressurized state, the coils 307 of the third variable chamber 306 are disposed at an angle 311 relative to an axis 328 that extends from the center 330 of the base 308 through the center 332 of the distal end 326 and through the center of the first inflatable structure 302. In the unpressurized state, the coils 303 of the second variable chamber 304 are disposed at an angle 315 relative to the axis 228. In this embodiment, the angles 311, 315 of the wrap for the coils 305, 307 may be chosen for the number of wraps desired, and may be up to about 90 degrees The first variable chamber 302 is defined by a boundary envelope 336 formed from a bendable material in the desired geometric shape. In this example the shape is generally that of a closed cylinder extending from the base 308. The material of the boundary envelope 336 is expandable/stretchable for reconfiguration purposes. The second variable chamber 304 is defined by a boundary envelope 338 formed from a bendable material in the desired geometric shape. The material of the boundary envelope 338 is also expandable/stretchable. The material examples listed above in describing FIGS. 1-3 are non-limiting examples for the boundary envelopes 336, 338 and 340 of this exemplary embodiment as well. In this example, the shape of the second variable chamber 304 is that of a tube spiraling around the first variable chamber 302 in a left-hand (as viewed), helix-like manner. The third variable chamber 306 is defined by a boundary envelope 340 formed from a bendable material in the desired geometric shape. In this example, the shape is that of a tube spiraling around the first variable chamber 302 in a left-hand (as viewed), helix-like manner. The material of the boundary envelope 340 is expandable/stretchable. The coils of the second and third variable chambers 304, 306 are staged along the length 334 of the first variable chamber 302 at the segments 305, 307 so that they do not overlap one another as they extend along the first variable chamber 302. In other embodiments, the staging of the second and third variable chambers 304, 306 is selected depending on the areas of the first variable chamber 302 to be restrained.

Deployment of the inflatable structure 300 may be initiated in a number of variations. For example, as illustrated in FIG. 14, the inflation system 28 as configured in FIG. 7 is used. The control valve 48 may be opened by the controller 62 to pressurize the second variable chamber 304. The third variable chamber 306 remains uninflated. The first variable chamber 302 may be inflated. Alternatively, the first variable chamber 302 may not be inflated but the pressure at the inside 312 may increase as a result of the action of the second variable chamber 304 due to its pressurization. Depending on the pressure level in variable chamber 304, and the amount of restraint that results, the transition segment 309 may be repositioned a greater distance from the proximal end 324 than their distance of separation in FIG. 13. The boundary envelopes 336 and 338 and the boundary envelopes 336 and 340 are in contact and may be fixed relative to each other to restrain the boundary envelope 336 during pressurization. As shown in FIG. 14, the inflatable structure 300 is inflated to a state where the segments 305 and 307 are transformed to different shapes than when in the unpressurized state of FIG. 13. The volume of the first variable chamber may remain substantially constant as the segment 307 expands. Through the construction the inflatable structure 300 a skeleton and flesh type paradigm is achieved where the second and third variable chambers 304, 306 provide the supportive skeleton and the first variable chamber 302 provides the skin/flesh. Hierarchical aspects include the relative volumes of the first variable chamber 302 to the second and third variable chambers 304, 206 as operative scales that may differ by an order of magnitude.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

What is claimed is:

1. An inflatable structure comprising:
   multiple variable chambers including a first variable chamber and a second variable chamber;
   a first boundary envelope defining the first variable chamber;
   a second boundary envelope defining the second variable chamber, the first and second boundary envelopes separating the first variable chamber from the second variable chamber;
   an inflation system configured to inflate the first variable chamber to a first pressure and to inflate the second variable chamber to a second pressure higher than the first pressure for a higher stiffness of the second boundary envelope as compared to the first boundary envelope; and
   a base configured as an interface between the inflation system and the first and second variable chambers, the base including a first nozzle in fluid communication with the first variable chamber and a second nozzle in fluid communication with the second variable chamber;
   wherein the first and second variable chambers are defined by an operative scale that differs by an order of magnitude between the first and second variable chambers;
   wherein the operative scale is volume with the first variable chamber defining a first volume when fully inflated and the second variable chamber defining a second volume when fully inflated, the second volume smaller than a first volume by the order of magnitude.

2. The inflatable structure of claim 1, comprising a controller configured to: monitor, by a first pressure sensor, a first pressure inside the first variable chamber; and monitor, by a second pressure sensor, a second pressure in the second variable chamber.

3. The inflatable structure of claim 2 comprising:
   a valve disposed to control inflation of the first variable chamber,
   wherein the controller is configured to: access a design pressure; and close the valve when the first pressure sensor indicates the first pressure equals a predetermined design pressure selected to maintain pressure and shape of the first variable chamber.

4. The inflatable structure of claim 1 wherein the second variable chamber is configured to be inflated before the first variable chamber so that the inflatable structure inflates to a substantially deployed state more quickly than if the first variable chamber were inflated first.

5. The inflatable structure of claim 1 wherein the inflatable structure is stored in a first state and is deployed in a second state, and wherein when in the first state the inflatable structure has a size that is compact relative to the second state.

6. The inflatable structure of claim 1 comprising:
   a third variable chamber; and
   a third boundary envelope defining the third variable chamber wherein the second and third boundary envelopes are in contact with the first boundary envelope.

7. The inflatable structure of claim 6 wherein the first chamber has a length and the second and third variable chambers both have helix shapes wrapped around the first variable chamber, the helix shapes of the second and third variable chambers wrapped along the length.

8. The inflatable structure of claim 6 wherein the first variable chamber extends along an axis, the second variable chamber is wrapped at a first angle relative to the axis, and the third variable chamber is wrapped at a second angle relative to the axis that differs from the first angle.

9. The inflatable structure of claim 1 comprising:
   a third variable chamber; and
   a third boundary envelope defining the third variable chamber, wherein the second and third boundary envelopes are fixed to the first boundary envelope so that when the second or third variable chamber is pressurized, the first variable chamber extends or contracts.

10. The inflatable structure of claim 1 wherein the first boundary envelope comprises a material that is stretchable so that the first boundary envelope is expanded when pressurized, and the second boundary envelope comprises a material that is non-stretchable so that the second boundary envelope is substantially non-expanded when pressurized.

11. A method of deploying an inflatable structure comprising:
    constructing the inflatable structure with multiple variable chambers including a first variable chamber and a second variable chamber, a first boundary envelope defining the first variable chamber; and a second boundary envelope defining the second variable chamber;
    constructing an inflation system to inflate the first variable chamber to a first pressure and to inflate the second variable chamber to a second pressure higher than the first pressure for a higher stiffness of the second boundary envelope as compared to the first boundary envelope;
    adding a base as an interface between the inflation system and the first and second variable chambers, the base including a first nozzle in fluid communication with the first variable chamber and a second nozzle in fluid communication with the second variable chamber;

separating the first variable chamber from the second variable chamber by the first and second boundary envelopes; and defining the first and second variable chambers by an operative scale that differs by an order of magnitude between the first and second variable chambers, wherein the operative scale is volume with the first variable chamber defining a first volume when fully inflated and the second variable chamber defining a second volume when fully inflated, the second volume smaller than a first volume by the order of magnitude.

12. The method of claim 11 comprising:
inflating, by an inflation system, the first variable chamber to a first pressure;
and
inflating, by the inflation system, the second variable chamber to a second pressure wherein the second pressure is higher than the first pressure so that the second boundary envelope is stiffer than the first boundary envelope and the second variable chamber supports the first variable chamber.

13. The method of claim 12 comprising:
inflating the second variable chamber before inflating the first variable chamber so that the inflatable structure inflates to a substantially deployed state more quickly than if the first variable chamber were inflated first.

14. The method of claim 11 comprising:
connecting a base with the first and second variable chambers, the base having a first nozzle open to the first variable chamber and a second nozzle open to the second variable chamber; and
selectively connecting a pressure source, by an inflation system, with the first and second nozzles.

15. The method of claim 11 comprising:
storing the inflatable structure in a first state; and
deploying the inflatable structure in a second state wherein when in the first state the inflatable structure has a size that is compact relative to the second state.

16. The method of claim 11 comprising:
providing a third variable chamber of the inflatable structure; and
constructing the second and third variable chambers with helix shapes wrapped around the first variable chamber.

17. The method of claim 16 comprising:
constructing the first variable chamber to extend and contract along an axis; and
constructing the second and third variable chambers so that the helix shape of the second variable chamber is wrapped at a first angle relative to the axis, and the helix shape of the third variable chamber is wrapped at a second angle relative to the axis that is different than the first angle.

18. The method of claim 16 comprising:
staging the second and third variable chambers along the first variable chamber in non-overlapping positions; and
defining a variable shape of the first variable chamber by varying pressure supplied to the second or third variable chambers while no internal pressure is supplied to the first variable chamber.

19. The method of claim 11 comprising:
constructing a third variable chamber of the inflatable structure defined by a third boundary envelope; and
constructing the inflatable structure so that the second and third boundary envelopes are fixed to the first boundary envelope.

20. An inflatable structure comprising:
multiple variable chambers including a first variable chamber and a second variable chamber;
a pressure source configured to inflate the inflatable structure;
a first conduit in fluid communication with the first variable chamber and with the pressure source;
a second conduit in fluid communication with the second variable chamber and with the pressure source;
an inflation system configured to inflate the first variable chamber through the first conduit and to inflate the second variable chamber through the second conduit;
a first pressure sensor disposed in the first conduit;
a first valve controlling flow through the first conduit;
a second pressure sensor disposed in the second conduit;
a second valve controlling flow through the second conduit;
a controller configured to operate the pressure source and the first and second valves in response to the first and second pressure sensors to inflate the first variable chamber to a first pressure and to inflate the second variable chamber to a second pressure;
a first boundary envelope defining a first volume of the first variable chamber;
a second boundary envelope defining a second volume of the second variable chamber, wherein the first volume is approximately ten times the second volume in magnitude; and
wherein the second pressure is greater than the first pressure so that multiple configurations of the inflatable structure or articulations are provided by selective pressurization of the multiple variable chambers.

* * * * *